(12) United States Patent
Eden

(10) Patent No.: US 6,197,576 B1
(45) Date of Patent: Mar. 6, 2001

(54) INSTRUMENT FOR DETECTION OF MICROORGANISMS

(76) Inventor: Gideon Eden, 2765 Ember Way, Ann Arbor, MI (US) 48104

( * ) Notice: Subject to any disclaimer, the term of this patent is extended or adjusted under 35 U.S.C. 154(b) by 0 days.

(21) Appl. No.: 09/317,477

(22) Filed: May 24, 1999

Related U.S. Application Data

(60) Provisional application No. 60/086,503, filed on May 22, 1998.

(51) Int. Cl.$^7$ ....................................................... C12M 1/34
(52) U.S. Cl. ...................... 435/288.7; 435/808; 356/436; 422/82.09
(58) Field of Search ................................ 435/288.7, 808; 250/328, 564, 573; 356/432, 434, 435, 436, 39, 246; 422/82.05–82.09

(56) References Cited

U.S. PATENT DOCUMENTS

| | | | |
|---|---|---|---|
| 3,773,426 | * 11/1973 | Mudd ................................... | 356/205 |
| 4,685,074 | * 8/1987 | May et al. ............................ | 364/564 |
| 4,857,944 | * 8/1989 | Hart et al. ............................ | 346/154 |
| 5,073,029 | * 12/1991 | Eberly et al. ........................ | 356/432 |
| 5,104,804 | * 4/1992 | Humphries et al. ................. | 435/291 |
| 5,164,796 | * 11/1992 | Di Guiseppi et al. ............... | 356/445 |
| 5,366,873 | * 11/1994 | Eden et al. ........................... | 435/34 |
| 5,427,920 | * 6/1995 | Berndt et al. ........................ | 435/34 |

* cited by examiner

Primary Examiner—William H. Beisner
(74) Attorney, Agent, or Firm—James M. Deimen

(57) ABSTRACT

An instrument to detect the presence of live microorganisms is described. The instrument is capable of providing simultaneous optical readings of multiple test vials containing different samples. Spectral variations due to metabolic activity of microorganisms are continuously recorded. An automated calibration scheme compensates for the parametric differences among the test vial locations.

5 Claims, 1 Drawing Sheet

INSTRUMENT FOR DETECTION OF MICROORGANISMS

CROSS REFERENCES TO RELATED APPLICATIONS

This application claims the benefit of U.S. Provisional Application No. 60/086,503, filed May 22, 1998.

The invention of this application is related to the invention of my U.S. Pat. No. 5,366,873, granted Nov. 22, 1994.

BACKGROUND

1. Field of Invention

The present invention relates to instruments for detecting microbial growth and, more particularly, relates to optical means to measure spectral changes of dyes due to metabolic activities of the microorganisms.

2. Description of Prior Art

It is desirable to test various industrial samples such as food, pharmaceuticals, cosmetics and water for microbial contamination. One area of biological testing of samples involves the estimation of the total number of bacteria, yeasts and molds as well as concentrations of specific groups of organisms within the material. One widely used method is known as the "standard plate count" method and involves culturing a diluted sample of product in an agar growth medium. The plates containing the sample and the growth medium are incubated for 24 hours to 5 days depending upon the assay. After incubation, colonies of microorganisms which have grown in the agar are counted.

Colorimetric methods have been successfully used to classify microorganisms in clinical samples. These methods are used with pure cultures Without interfering substances. In actual industrial samples, however, solid material can mask the optical signal yielding poor signal to noise ratio of the detection system. In order to resolve this problem a special vial configuration was designed. U.S. Pat. No. 5,366,873 to Gideon Eden and Ruth Eden (Nov. 22, 1994) discloses a device for detecting microbial growth from a sample substance wherein the device includes a container which is at least partially transparent. A fluid layer is disposed in a container for cultivating microorganisms therein. An indicator substance is disposed in the fluid layer for undergoing transformation in the presence of microorganism growth. A barrier layer is disposed in the container which is a semi fluid substance, the fluid portion of which is the same composition as the fluid layer in which the microorganisms are cultivated. Therefore the fluid in the semifluid layer is in equilibrium with the fluid layer. The semifluid substance provides a barrier to solid substances introduced into the fluid layer while providing a zone within which changes in the indicator substance due to microbial growth can be detected.

The patent also discloses an embodiment of an instrument comprising a light source positioned at the bottom part of the container such that the transmitted light is directed through the transparent part of the vial and the barrier layer. A simple and inexpensive light source is a Light Emitting Diode (LED) which is available in various wavelengths in the range of red, orange, yellow, green and blue spectra. The LEDs are controlled by a controller which provides stable electrical energy.

Light Emitting Diodes are quite desirable for specific applications. If a limited number of discrete spectrum bands need be measured, then LED's can be adequately utilized, especially in situations where multiple samples are measured simultaneously. Rather than using a mechanical indexing system, in which a single light source (as well as a single detector) travels to each sample location, one can provide a dedicated light source (as well as a dedicated detector) located in each sample's position. LED's are reliable devices, quite inexpensive and can provide long t;me operation, eliminating expensive and fragile mechanical apparatus. There are, however, serious disadvantages to LED's when utilized in commercial systems. Most of the problems are associated with their scattered parameters. When using commercial LED's, which are manufactured in huge quantities, it is common to find LED's which differ widely in their light characteristics. Differences of up to 50% of light energy can be found in "identical" LED's. The transmitted light angle can also vary considerably, changing the distribution of light at specific angles. In addition the LED/sensor combined characteristics may vary, depending upon the relative position in which they are mounted. U.S. Pat. No. 5,164,796 to James L. Di Guiseppi and Thurman C. Thorpe (Nov. 17, 1992) attempts to correct these differences by employing a stabilized current source connected to a serial combination of groups of LED's. While identical current applied to different LED's can reduce the light variations it still can result in significant differences. In addition, this arrangement cannot compensate for the angle differences and the mounting variations among the different locations.

SUMMARY OBJECTS AND ADVANTAGES

Accordingly, several objects and advantages of my invention are to provide an instrument which utilizes commercial LED's, and a corresponding method to compensate for their inherent differences. Another objective is to provide a "self calibration" scheme that the user can apply periodically with or without standard reference vials.

Still further objects and advantages will become apparent from a consideration of the ensuing description and accompanying drawings.

PREFERRED EMBODIMENT—DESCRIPTION

Figure 1:
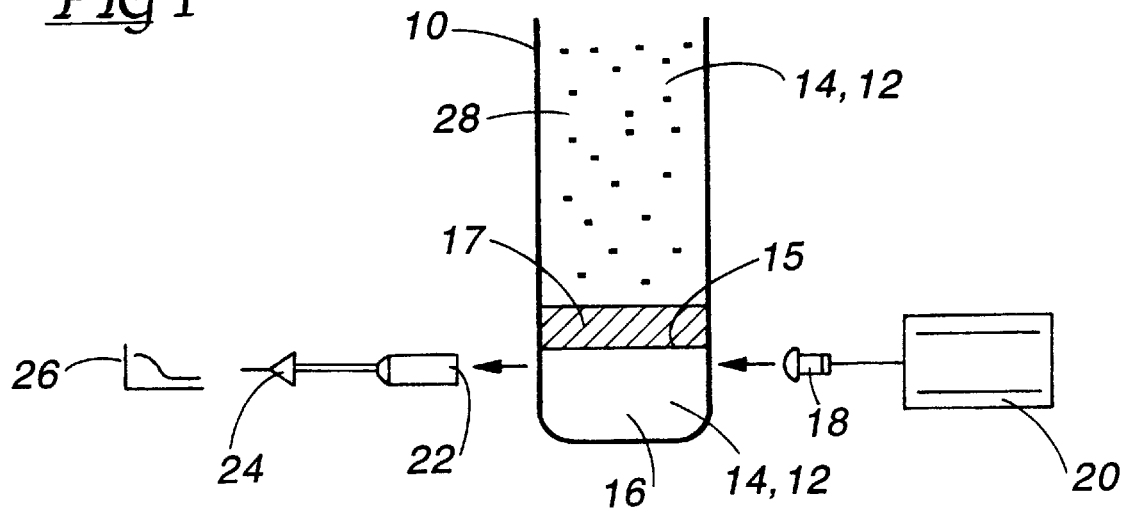
FIG. 1 shows specific components of the system described in the prior art.

FIG. 1 illustrates a typical configuration of the various components of a system which can be utilized in accordance with this invention. The vial 10 is made of transparent material. The barrier layer 16 may be composed of any available agar and non toxic dye 14. A separate sterile mixture of liquid media 12 and dye 14 is poured on top of the barrier layer 16. The tested sample 28 is placed in the fluid layer 12,14 and the vial 10 is placed in an incubating device, at an appropriate temperature, to promote the growth of organisms. A light source 18 is positioned at the bottom part of the vial 10, such that the transmitted light is directed through the transparent walls of the vial 10 and the barrier layer 16. In the preferred embodiment a Light Emitting Diode is utilized as the light source 18. In other embodiments, other light sources can be used; such as incandescent lamps, gas discharged lamps, lasers, or combinations of any light source with fiber optic means to transfer the light energy from the light source to any vial's position.

The dynamic changes of the transmitted light, which is the indicator for bacterial activity, is converted to electrical energy utilizing a light sensor 22 and amplifier 24. Although a wide variety of sensors may be utilized, e.g., photo voltaic, photo diodes, photo transistors, photo multipliers, charged coupled devices (CCD) and multi-channel devices, low cost solid state sensors can be employed due to the high energy of light reaching the sensor. Therefore, each vial can have its own pair of light source and sensor eliminating complex mechanical indexing devices utilized in optical readers, thereby increasing the reliability and the operating life of the instrument.

As previously discussed, the problem with multiplicity of pairs of light sources and light sensors is the variability amongst the various locations. In other words the same vial may yield different readings in different locations. This problem is considerably enhanced when utilizing LED's which can differ in their intrinsic mechanical and electrical characteristics. One of the ways to overcome this problem can be accomplished during the manufacturing of the instrument. The light source components should be carefully chosen to have identical parameters. The same matching procedure should be applied to the light detectors as well. Mounting of the light sources and the light detectors is also critical since the same amount of energy should reach the light sensor under identical light conditions. Any variation of the angle in which light is transmitted from the light source will result in a different reading. Practically this solution is very expensive and does not ensure proper operation for a long period of time without periodical re-adjustments.

Figure 2:
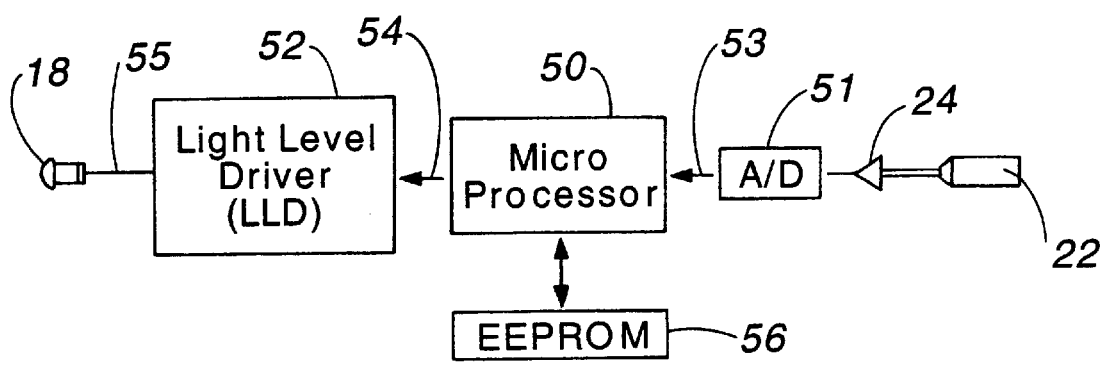
FIG. 2 shows a block diagram of the preferred embodiment of the system.

The alternative approach is illustrated in the preferred embodiment shown in FIG. 2. A microprocessor 50 is used to provide the calibration scheme as well as control of the individual light sources during normal operation. A digital input line 53 feeds the microprocessor 50 with the light level obtained from each vial 10 and sensor 22 location and the signal is converted to digital data by an Analog to Digital (AND) converter 51. The microprocessor 50 has a digital output 54 which controls the brightness of the light source 18 by converting the digital output to energy level generated by a Light Level Driver (LLD) 52. The LLD 52 determines the required light energy by converting the digital data present at output line 54 to an analog level and providing electrical power, related to the analog level, to the light source 18 via a power line 55. In its simplest form the LLD 52 can be constructed from a Digital to Analog (D/A) converter and a power driver such as a Field Effect Transistor (FET) which provides energy proportional to the voltage generated by the D/A converter.

An electrically erasable memory (EEPROM) 56 is controlled by the microprocessor 50 which can write and/or read parameter values from the memory. The EEPROM 56 is used to store individual light levels for each location and individual calibration parameters. Internally, the microprocessor 50 has a software program which provides the calibration and the reading algorithms, described below.

In the preferred embodiment the system is "self calibrating" without employing any standard reference vials. During the calibration process the following steps are carried out:

1. Establishing a light threshold TH common to all vial locations. This level is measured at the A/D output line 53. The threshold level TH compensates for all variations between the locations due to the variability among the light sources and the light detectors. It also compensates for the variability of mechanical mounting characteristics of the locations.

2. Determining the Open Position (OP) and the Open Level (OL) for each location. These levels are obtained when the vial is taken out of the system, and the light generated from the light source 18 travels through air and hits the light sensor 22 without the influence of the dye. To determine the individual OP and OL the microprocessor generates, following internal program instructions, increasing levels of energy by incrementing the numbers at the output line 54 which controls the energy level generated by the LLD 52, and consequently increasing the brightness of the light source 18. The gradual energy change is recorded by the light detector 22 and fed back to the microprocessor via the A/D converter 51. The incremental change is repeated until the threshold TH, described above, has been exceeded. At this point the increment value is recorded as the individual OP, and the actual level exceeding the threshold TH is recorded as the individual OL. The OP and OL values are stored in the EEPROM 56 for each location.

3. Establishing a Low Level Position (LLP) for each location. This level generates energy from the LLD corresponding to the lowest possible expected energy level measured upon dynamic signals obtained with actual test samples. In other words the LLP can be regarded as a simulated value of a standard reference of the lowest possible level. The simulated level eliminates the need to employ actual vials containing standard dyes during the calibration process.

One way to establish the LLP is to utilize a specific fraction of the OP which represents the standard. As an example, one fifth of the individual OP can be used as the individual LLP. This fraction is heavily dependent of the dyes utilized as well as their initial concentrations.

4. Determining the individual Low Level (LL) for each location. This level is obtained by driving each location to its individual LLP and recording the corresponding value at line 53. The individual LL of each location is stored in the EEPROM.

The procedure described in steps 1 to 4 represent the calibration process of the preferred embodiment. Since no standard vials are utilized, the system can be programmed to perform an automatic "self calibration" procedure based upon these steps.

During normal operation of the system, the stored calibration parameters in the EEPROM can be used in conjunction with the actual reading according to the following scheme:

a. For each location the microprocessor 50 sets the LED energy to its OP level by setting the output line 54 to that level.
 b. The light sensor 22 reads the actual level X from the vial, generated at the output line 53 of the A/D 51.
 c. The microprocessor 50 adjusts the value X, according to the calibration parameters using the following formula:

$$Y=X(U-L)/(OL-LL)+U-OL(U-L)/(OL-LL)$$

Where U and L are the desired values for the high (no vial) signal and the desired value for the lowest value respectively. For example, if a percentage scale is desirable then U can be set to 100 and L can be set to 10. Consequently, the signal will follow a pattern which may have a low value close to 10 and will never exceed the open 100 value.

CONCLUSIONS, RAMIFICATIONS, AND SCOPE

Accordingly, it can be seen that a self calibrating instrument for the detection of microorganisms can be accomplished. The calibration scheme combines the effect of all the differences among the multiple locations and eliminates these differences by (a) driving the light sources to similar readings under open conditions (no vials), (b) simulating low levels for each individual location and (C) applying a calibration formula for the actual readings.

Although the description above contains many specificities, these should not be construed as limiting the scope of the invention but as merely providing illustrations of some of the presently preferred embodiments of this invention. Various other embodiments and ramifications are possible within its scope. For example, the light source may be different than a simple LED. Incandescent lamps, fiber optics or any other multiple light sources can utilize the same principles. In addition various light detectors such as photo diodes, photo transistors, photo-voltaic devices or video cameras can be used. Finally either reflectance, transmittance or fluorescence signal systems can use this compensation scheme.

Another embodiment which can be utilized employs physical standard vials which replace the simulated LLP. Rather than calculating the LLP and reading the corresponding LL, it is possible to directly read the LL from the standard vial while the LED is set to the OP level. The rest of the calibration scheme and actual reading and adjustment remain unchanged.

Thus the scope of the invention should be determined by the appended claims and their legal equivalents, rather than by the examples given.

What is claimed is:

1. An instrument for detecting microbial growth in test vials containing growth media and dye material, comprising:
    a multiplicity of light-sensor combinations, each combination comprising at least one light source and at least one light detector positioned at the location of each of the test vials, said light detector positioned relative to said light sensor to detect light emitted from the dye material when said light source illuminates said dye material;
    calibration means for compensating differences among the output values of said light detector for each said combination, said calibration means providing similar output levels of said light detectors for said test vials having identical compositions of said media and said dye material;
    a driver means for separately driving each said light source at a specific energy level;
    a processor means for controlling said driver means;
    an algorithm embedded in said processor means, providing compensated output values of said light detectors and applying a mathematical transformation to the output of said light detectors, to reduce parametric differences among the output values of said light detectors resulting from the combined performance differences among said light source and light detector combinations;
    said algorithm comprising the formula:

$$Y=X(U-L)/(OL-LL)+U-OL(U-L)/(OL-LL)$$

Wherein:
    X is the output from said light source;
    Y is said compensated value;
    U is a desired maximal level common to all said compensated levels;
    L is a desired minimal level common to all said compensated levels;
    OL is the output of said light detector receiving energy directly from said light source when said test vial is being removed; and
    LL is the output of said light detector when said light source is driven by said driver means at a level representing the minimal energy obtained from said light detector for any of said test vials.

2. The instrument as in claim 1 wherein said light source is a light emitting diode.

3. The instrument as in claim 1 wherein said light source is an incandescent lamp.

4. The instrument as in claim 1 wherein each of said light source comprises a fiber optics transferring light from a central light source to at least one of said test vials.

5. The instrument of claim 1 wherein each of said light sources is driven by said driver means to the same level TH measured at the output of said light detector when said test vial is removed thereby compensating for intrinsic parametric differences among said light sources and among said light detectors, and differences resulting from the combined performance, due to mechanical mounting processes and optical differences of said combinations of said light sources and light detectors.

* * * * *